United States Patent [19]

Radnoti

[11] 4,016,063
[45] Apr. 5, 1977

[54] ELECTRODE SHIELD

[76] Inventor: Desmond Arpad Radnoti, 670 Alta Vista, Sierra Madre, Calif. 91024

[22] Filed: Aug. 6, 1975

[21] Appl. No.: 602,407

[52] U.S. Cl. .................... 204/195 R; 204/195 G
[51] Int. Cl.² ........................................ G01N 27/36
[58] Field of Search ............ 204/195 G, 1 H, 282, 204/195 R, 279, 195 F; 324/30 R

[56] References Cited

UNITED STATES PATENTS

| 1,373,951 | 4/1921 | Cox et al. | 324/30 R X |
| 1,524,937 | 2/1925 | Keeler | 324/30 R X |
| 1,951,035 | 3/1934 | Parker | 204/195 R X |
| 2,563,062 | 8/1951 | Perley | 204/195 G |
| 2,755,243 | 7/1956 | Beckman et al. | 204/195 G |
| 3,652,439 | 3/1972 | Ben-Yaakov et al. | 204/195 R |

*Primary Examiner*—G. L. Kaplan
*Attorney, Agent, or Firm*—Witherspoon, Lane & Hargest

[57] ABSTRACT

An electrode shield for protecting the fragile part or parts of a measuring electrode when said electrode is being utilized is disclosed. The shield is so designed that it provides protection to the fragile electrode without interfering with the functioning of the electrode.

6 Claims, 5 Drawing Figures

ELECTRODE SHIELD

BACKGROUND OF THE INVENTION

This invention relates to electrode shields; and more particularly, to an electrode shield that provides protection against the breakage of fragile electrodes without interfering with the functioning of the electrodes.

In some monitoring and/or measuring procedures electrodes having a fragile part or parts are utilized. For example, in PH measurements, fragile glass electrodes are often utilized. In use, such a fragile electrode is exposed to many hazards which frequently result in breakage of the electrode, requiring costly replacement and delay of operations. For example in making PH measurements, the electrode may be exposed to hard particles that are accelerated in the media due to stirring or the like. These hard particles can, and often do, strike the fragile part or parts of the electrode with sufficient force to break the electrode.

In order to protect such fragile electrodes some form of shield is required. However, the shield must be so designed and constructed that the shield does not interfere with the operation of the electrode. This invention provides an electrode shield that minimizes the hazards to which fragile electrodes are exposed during use without interfering with the operation of the electrode.

SUMMARY OF THE INVENTION

The invention comprises an electrode shield that envelopes the fragile part or parts of the electrodes to provide physical protection. Vents are provided in the shield to expose the electrode to it's medium of operation in such a manner that the function of the electrode is not impaired by the shield. Thus, the shield provides physical protection without interfering with the functioning of the electrode. Means are provided to readily secure and remove the shield to and from the electrode. When the electrode is not in use it is removed from the shield and stored in a protective container. A suitable storage container is also disclosed herein.

BRIEF DESCRIPTION OF THE DRAWING

A complete understanding of the exact nature and structural details of the invention can be obtained from the following detailed description of the invention when read in conjunction with the annexed drawing in which.

DETAILED DESCRIPTION OF THE INVENTION

Figure 1:
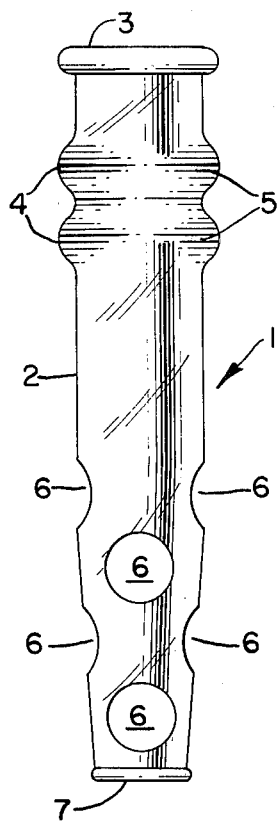
FIG. 1 shows a first embodiment of the electrode shield of the invention.

Referring first to FIG. 1, this Figure shows a first embodiment of the electrode shield of this invention. As shown in FIG. 1, the shield 1 has a generally cylindrical shaped hollow body 2. Hollow body 2 is preferably made of glass or other suitable inert material. Hollow body 2 has an opening or lip 3 formed at the top end thereof. A short distance below opening 3, body 2 has a pair of spaced apart protusion 4. These protusions 4 are fabricated into body 2 to accommodate and hold in place a pair of sealing rings 5. Sealing rings 5 are made of any suitable inert material. A plurality of circular openings 6 are formed in body 2 as shown. A circular opening 7 is also formed in the bottom end of body 2. Lip or opening 3, openings 6 and opening 7 are all preferably fired to provide smoothly rounded edges.

Figure 2:
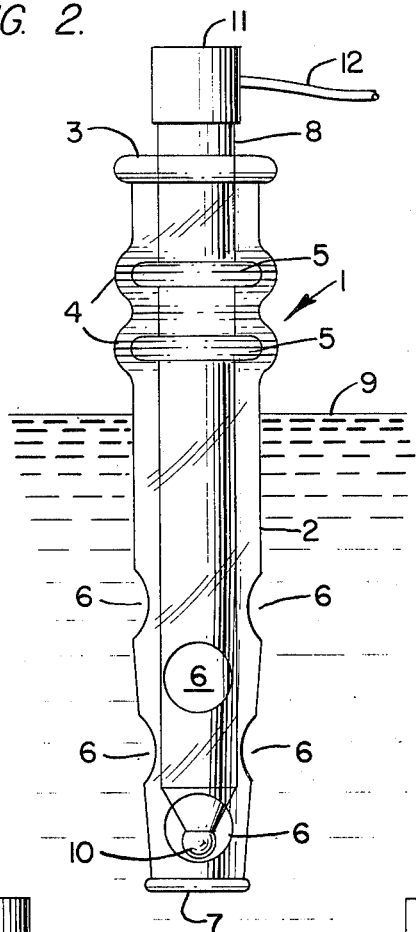
FIG. 2 shows an electrode inserted into the shield of FIG. 1 and immersed in a liquid.

Referring now to FIG. 2, the Figure shows the shield 1 of FIG. 1 immersed in a liquid 9 with an electrode probe 8 inserted into shield 1. Sealing rings 5 provide a cushion for electrode 8 and frictionally hold electrode 8 in place inside shield 1. The inside diameter of rings 5 is such that electrode 8 fits snugly inside rings 5. Rings 5 are slightly resilient and frictionally grip the body of electrode 8. Electrode 8 has a highly fragile ball tip 10 at the bottom end and an end cap 11 at the top end. An electrical lead or leads 12 emanate from end cap 11.

Liquid 9 may and very often does contain particles. These particles may be very minute. However, even these minute particles may be accelerated with considerable force if liquid 9 turbulent as is often the case. For example, in some instances it is necessary to agitate liquid 9 thereby causing turbulence. Tip 10 is very fragile and can be broken by the impact of these hard particles, particularly when the particles are accelerated through the liquid. Even minute particles can break tip 10. Thus, when electrode 8 is immersed in liquid 9 without any protection, the risk of breaking tip 10 is very high. Further, tip 10 can be rather easily broken by striking the bottom or sides of the container holding liquid 9. Liquid 9 is, of course, contained in some type of container.

Shield 1 protects against the breakage of tip 10 by hard particles and the like and also protects against the breakage of tip 10 by the striking of the bottom or sides of a container with tip 10 without interfering with the operation of electrode 8. Openings 6 and opening 7 permit liquid 9 to enter shield 10 to expose tip 10 to liquid 9. However, openings 6 and opening 7 are so positioned relative to tip 10 that the chances of an impact of tip 10 by a hard particle are very remote. Thus, electrode 8 can measure and/or monitor liquid 9 without being subjected to the hazards that are encountered by an unshielded electrode. Further, tip 10 is protected against any accidental impact of tip 10 against the bottom or sides of the container holding liquid 9.

Figure 3:
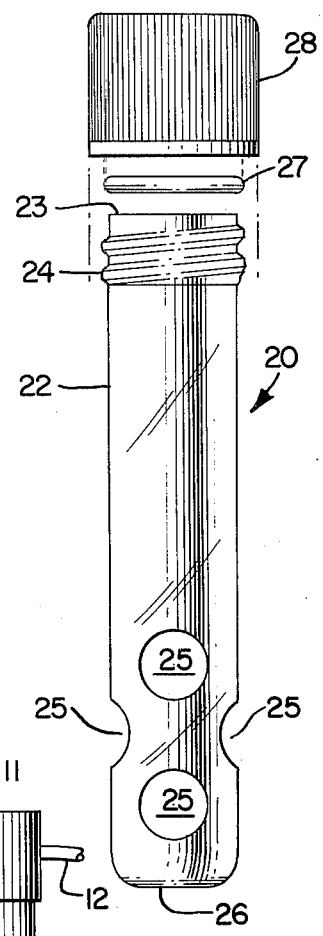
FIG. 3 shows a second embodiment of the electrode shield of this invention.
Figure 4:
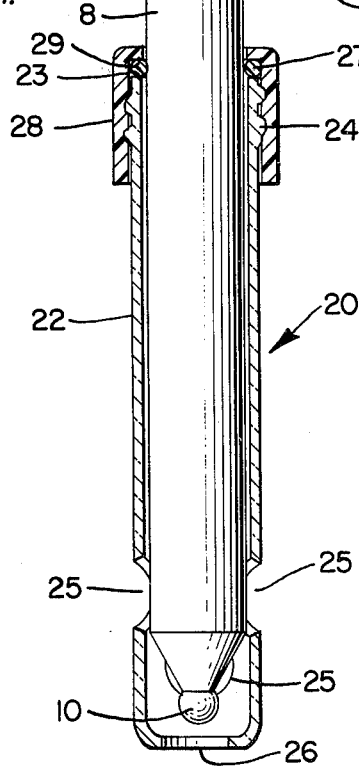
FIG. 4 shows the shield of FIG. 3 in cross-section with an electrode inserted into the shield.

FIG. 3 shows a second embodiment of the invention. As shown in this Figure, the shield 20 comprises a hollow generally cylindrical body 22 made of glass or other suitable material. Hollow body 2 has a plurality of generally circular shaped holes 25 as shown in FIG. 3 and a generally circular shaped hole 26 in the bottom end. An opening 23 is provided in the top of body 22 and threads 24 are provided adjacent opening 23. Shield 20 also includes a sealing ring 27 and a cap 28. As shown in FIG. 4, cap 28 has internal threads that mate with threads 24 to secure cap 28 to body 22. Cap 28 also has a circular opening in the top thereof as is apparent in FIG. 4.

FIG. 4 shows shield 20 in cross-section with electrode 8 inserted into shield 20. As shown in FIG. 4, sealing ring 27 rests on top of body 22 and is pressed down onto the top of body 22 by a flange 29 provided at the top of cap 28 when cap 28 is tightly threaded onto body 22. Electrode 8 passes through cap 28 and sealing ring 27 down into body 22 as shown in FIG. 4. Sealing ring 27 provides a cushioning effect on electrode 8 and frictionally holds electrode 8 in place when it is inserted into body 22 of shield 20.

As was the case with shield 1 of FIGS. 1 and 2, when shield 20 is placed in a liquid with electrode 8 inserted into shield 20, holes 25 and hole 26 permit intimate contact of the liquid with tip 10 while shield 20 protects tip 10 from impact by hard particles and the like. Further, shield 20 also protects tip 10 against any accidental impact with the container holding the liquid being measured.

Figure 5:
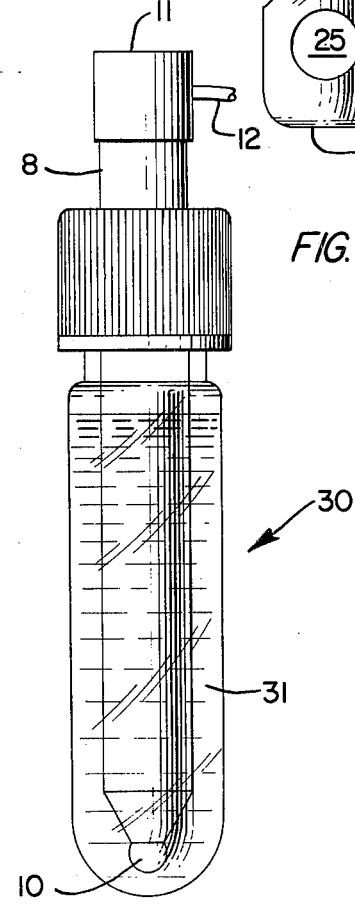
FIG. 5 shows the electrode stored in a protective container when not in use.

When electrodes such as electrode 8 are not being used, such electrodes should, of course, be stored in a protective container to prevent breakage. In addition, such electrodes are preferably immersed in a liquid, for example water, when stored to prevent the drying out of the electrode. FIG. 5 shows a container that is ideally suited for storing electrode 8 particularly when shield 20 is provided as the shield when electrode 8 is being utilized. As shown in FIG. 5, container 30 is a generally cylindrical container made of glass or other suitable material. A liquid 31 such as water is stored in container 30 with electrode 8 partially immersed in the liquid 31 when electrode 8 is inserted into container 30. The top part of electrode 8 need not be immersed in a liquid and is not fragile. Container 30 is provided with threads, not shown, of such size as to accommodate cap 28 of shield 20. Thus, when one is finished using electrode 8, he merely unscrews cap 28 from shield 20, inserts electrode 8 into container 30 and secures cap 28 to container 30. When so stored in container 30, sealing ring 27, not visible in FIG. 5, again holds electrode 8 in place and provides cushioning. In addition, sealing ring 27 provides a liquid tight seal to prevent the spillage of liquid 31 through the top of cap 28.

While container 30 is designed to accommodate cap 28 of shield 20, it should be obvious that container 30 can also be used to store electrode 8 when the shield utilized is shield 1 of FIG. 1 and 2. In this case, container 30 is provided with a cap and sealing ring such as cap 28 and sealing ring 27. Of course the cap and sealing ring need not be used with shield 1. It should also be obvious that shields 1 and 20 can be used with other types of electrodes than electrode 8. In other words shield 1 and 20 are not limited in usage to electrode 8. Electrode 8 is a type of electrode commercially available on the market. Other similar electrodes having a fragile part or parts are also available on the market and shields 1 and 20 can be used with these electrodes.

While the invention has been described with reference to specific embodiments it will be obvious that various changes and modifications can be made to the embodiments shown and described without departing from the spirit and scope of the invention as set forth in the claims.

What is claimed is:

1. An electrode shield for housing and protecting an electrode, said shield comprising:
   a hollow generally cylindrical shaped body having an opening at the top end thereof for receiving said electrode, an opening at the bottom end thereof smaller than said opening at said top end, a plurality of openings spaced apart along a portion of the wall thereof from said bottom end, a first recess formed in said wall below said opening and second recess formed in said wall below said first recess;
   a first sealing ring housed in said first recess and extending into the inside of said hollow body beyond the inner surface of said hollow body; and
   a second sealing ring housed in said second recess and extending into the inside of said hollow body beyond the inside surface of said hollow body, said first and said second sealing rings providing means for cushioning and frictionally holding said electrode in place when said electrode is inserted into said hollow body.

2. An electrode shield as defined in claim 1 wherein said plurality of holes are so spaced along said wall of said hollow body that the uppermost holes of said plurality of holes extend only a part way up said wall of said hollow body from said bottom end of said hollow body and are so spaced that while permitting liquid flow through said hollow body also protect the fragile portion of an electrode, when said electrode is inserted in said hollow body, from harmful impact by any particles in said liquid.

3. An electrode shield as defined in claim 2 wherein said hollow body is made of glass.

4. An electrode shield for housing an electrode, said shield comprising:
   A hollow generally cylindrical shaped body having an opening at the top end thereof for receiving said electrode, an opening at the bottom end thereof smaller than said opening at said top end, a plurality of openings in the wall of said hollow body, said plurality of openings being spaced apart from said bottom end, and external threads formed adjacent said top end;
   A cap being open at both ends and having internal threads for engaging said external threads of said hollow body to removably secure said cap to said hollow body; and
   A sealing ring nested inside of said cap such that said sealing ring is compressed against the top end of said hollow body at the inside of said cap, said sealing ring providing cushioning means and means to frictionally hold said electrode in place when said electrode is slipped through said cap into said hollow body.

5. An electrode shield as defined in claim 4 wherein said plurality of holes are so spaced along said wall of said hollow body that the uppermost holes of said plurality of holes extend only a part way up said wall of said hollow body from said bottom end of said hollow body and are so spaced that while permitting liquid flow through said hollow body also protect the fragile portion of an electrode, when said electrode is inserted in said hollow body, from harmful impact by any particles in said liquid.

6. An electrode shield as defined in claim 5 wherein said hollow body is made of glass.

* * * * *